United States Patent
Ogawa et al.

(10) Patent No.: US 9,968,563 B2
(45) Date of Patent: May 15, 2018

(54) MICROCAPSULE FORMULATION AND METHOD FOR PRODUCING THE SAME

(71) Applicants: JGC CORPORATION, Tokyo (JP); INDUSTRIAL TECHNOLOGY RESEARCH INSTITUTE, Hsinchu (TW)

(72) Inventors: Yasuaki Ogawa, Kyoto (JP); Naoki Tahara, Kanagawa (JP); Tomoya Yamashita, Kanagawa (JP); Shuzo Kojima, Kanagawa (JP); Felice Cheng, Hsinchu (TW); Sung-En Chen, Hsinchu (TW); Jui-Mei Lu, Hsinchu (TW)

(73) Assignees: JGC CORPORATION, Tokyo (JP); INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days. days.

(21) Appl. No.: 15/187,385

(22) Filed: Jun. 20, 2016

(65) Prior Publication Data
US 2017/0056330 A1    Mar. 2, 2017

(30) Foreign Application Priority Data
Sep. 1, 2015  (JP) .................................. 2015-171786

(51) Int. Cl.
*A61K 9/50* (2006.01)
*A61K 38/17* (2006.01)
(Continued)

(52) U.S. Cl.
CPC .............. *A61K 9/5089* (2013.01); *A61K 9/19* (2013.01); *A61K 9/50* (2013.01); *A61K 9/5015* (2013.01);
(Continued)

(58) Field of Classification Search
None
See application file for complete search history.

(56) References Cited

U.S. PATENT DOCUMENTS 6,083,534 A    7/2000 Wallach et al.
6,087,324 A *  7/2000 Igari .................... A61K 9/0019
                                                              424/499
(Continued)

FOREIGN PATENT DOCUMENTS

CN    1157562 A    8/1997
EP    0442671 A2   8/1991
(Continued)

OTHER PUBLICATIONS

Resomer Biodegradable Polymers for medical Device Applications Research, Sigma Aldrich, accessed Jul. 26, 2017).*
(Continued)

*Primary Examiner* — Robert A Wax
*Assistant Examiner* — Melissa S Mercier
(74) *Attorney, Agent, or Firm* — MH2 Technology Law Group, LLP

(57) ABSTRACT

An object of the present invention is to provide a method for producing a microcapsule formulation using a biodegradable polymer, the method being capable of avoiding direct contact of a peptidic physiologically active substance with an organic solvent layer, and achieving a high encapsulation efficiency of the peptidic physiologically active substance.

15 Claims, 1 Drawing Sheet

Example 1

Example 4

(51) Int. Cl.
*A61K 9/19* (2006.01)
*A61K 38/00* (2006.01)

(52) U.S. Cl.
CPC .......... *A61K 9/5026* (2013.01); *A61K 9/5031* (2013.01); *A61K 38/1793* (2013.01); *A61K 38/00* (2013.01)

(56) References Cited

U.S. PATENT DOCUMENTS

| | | | |
|---|---|---|---|
| 2004/0241229 A1 | 12/2004 | Yamamoto et al. | |
| 2015/0164815 A1* | 6/2015 | Loo .................... | A61K 9/0065 424/452 |

FOREIGN PATENT DOCUMENTS

| | | | | |
|---|---|---|---|---|
| EP | 0891774 | A2 | 1/1999 | |
| JP | H08-151321 | A | 6/1996 | |
| JP | H08-217691 | A | 8/1996 | |
| JP | 2002-255857 | A | 9/2002 | |
| JP | 3862304 | B2 | 12/2006 | |
| WO | 9607399 | A1 | 3/1996 | |
| WO | 2005/110369 | A2 | 11/2005 | |
| WO | 2012/071013 | A1 | 5/2012 | |
| WO | WO 2013059406 | A1 * | 4/2013 | ....... A61K 39/39591 |

OTHER PUBLICATIONS

Extended European Search Report dated Aug. 1, 2016 for European Patent Application No. 16175343.9, 9 pages.
Lisbeth Illum, "Nasal drug delivery: new developments and strategies", Drug Discovery Today, 2002, vol. 7, No. 23, pp. 1184-1189.
Lisbeth Illum, "Nasal drug delivery—possibilities, problems and solutions", Journal of Controlled Release, 2003, vol. 87, pp. 187-198.
Marquette et al., "Encapsulation of immunoglobulin G by solid-in-oil-in-water: Effect of process parameters on microsphere properties", European Journal of Pharmaceutics and Biopharmaceutics, 2014, vol. 86, pp. 393-403.
Johnson et al., "The Stabilization and Encapsulation of Human Growth Hormone into Biodegradable Microspheres", Pharmaceutical Research, 1997, vol. 14, No. 6, pp. 730-735.
Hongkee Sah, "Protein behavior at the water/methylene chloride interface", Journal of Pharmaceutical Science, 1999, vol. 88, No. 12, pp. 1320-1325.
Chen et al., "A multicenter open-label phase I/II study to assess the safety, tolerability, and efficacy of three dose levels of TuNEX in patients with rheumatoid arthritis", Journal of the Chinese Medical Association, 2011, vol. 74, pp. 544-551.

* cited by examiner

Example 1          Example 4

MICROCAPSULE FORMULATION AND METHOD FOR PRODUCING THE SAME

CROSS-REFERENCE TO RELATED APPLICATIONS

This application claims priority to Japanese Application No. 2015-171786 filed 1 Sep. 2015, the entire disclosure of which is hereby incorporated by reference in its entirety.

TECHNICAL FIELD

The present invention relates to a method for producing a microcapsule formulation containing a peptidic physiologically active substance, and a method for producing the microcapsule formulation.

BACKGROUND ART

Peptidic physiologically active substances, such as hormones, cytokines, hematopoietic factors, growth factors, enzymes, soluble or solubilized receptors, antibodies, peptidic antigens, blood coagulation factors, or adhesion factors, are mainly administered in the form of, for example, an injection by a parenteral administration method in view of the ease of being digested with in vivo digestive enzymes, hydrophilicity, instability, etc. The administration by injection accompanies pain upon administration. Therefore, from the viewpoint of improving QOL (quality of life) and increasing compliance, making physiological active substances as mentioned above or the like into sustained release formulations has been desired to extend administration intervals and avoid frequent administration (Non-patent Literature (NPL) 1 and 2).

As a means for technically solving this problem, numerous studies have been reported on sustained release microcapsule formulations containing a protein having a physiologically active effect and/or a pharmacologically active effect. For example, Patent Literature (PTL) 1 discloses a microcapsule comprising an amorphous water-soluble physiologically active substance and a high-molecular-weight polymer. PTL 1 discloses in the Examples that an amorphous antiplatelet drug (S)-4-[(4-amidinobenzoyl)glycyl]-3-methoxycarbonylmethyl-2-oxopiperazine-1-acetic acid is dispersed in a dichloromethane solution of a lactic acid-glycolic acid copolymer in which L-arginine has been dissolved, and the dispersion is finely divided into particles with a polytron and then formed into an S/O/W emulsion in an aqueous sodium chloride solution.

PTL 2 further discloses a sustained release formulation comprising a physiologically active substance-containing matrix and a cationic substance and/or a polyol, the formulation being capable of suppressing the initial release of the physiologically active substance. PTL 2 discloses that a powder (a Solid phase) obtained by freeze-drying a physiologically active substance solution is dispersed in a solution of a biologically active polymer in an organic solvent (an Oil phase), and the resulting S/O dispersion is added to an aqueous solvent (a Water phase) to produce an S/O/W emulsion.

In addition to the above, there are many reports on sustained release microcapsule formulations comprising a protein having a physiologically active effect and/or a pharmacologically active effect (PTL 3, PTL 4, NPL 3, and NPL 4).

CITATION LIST

Patent Literature

PTL 1: JPH08-151321A
PTL 2: JP2002-255857A
PTL 3: U.S. Pat. No. 6,083,534
PTL 4: JPH08-217691A

Non-Patent Literature

NPL 1: Drug Discovery Today. 7; 1184-1189 (2002)
NPL 2: J. Control. Rel. 87; 187-198 (2003)
NPL 3: European Journal of Pharmaceutics and Biopharmaceutics, 86; 393-403 (2014)
NPL 4: Pharmaceutical Research, 14; 730-735 (1997)
NPL 5: Journal of Pharmaceutical Science, 88; 1320-1325 (1999)
NPL 6: Journal of the Chinese Medical Association, 74; 544-551 (2011)

SUMMARY OF INVENTION

Technical Problem

In the above technique, an oil-water interface is formed in the step of dispersing a PLA- or PLGA-containing oil phase in a water phase. Therefore, there is a possibility that torsion may occur between the peripheral portion and the inside of the protein to disrupt the tertiary structure and cause denaturation, thus resulting in a failure to exert physiologically active effects (NPL 5). Accordingly, a method that can avoid denaturation of a peptidic physiologically active substance to the oil-water interface is desirable. A production method that has a high encapsulation efficiency for a peptidic physiologically active substance is considered to have high technical utility. Further, a method for producing a microcapsule formulation that releases a peptidic physiologically active substance at an almost constant rate is more desirable.

Solution to Problem

In view of the above problem, the present inventors conducted extensive research, and found that when a method comprises the steps of: preparing an amino acid-containing S/W suspension by adding a basic amino acid to an aqueous solvent containing a heavy metal salt of a peptidic physiologically active substance; dispersing the amino acid-containing S/W suspension in an amino acid-containing polymer solution containing a basic amino acid and a biodegradable polymer to form an S/W/O emulsion; dispersing the S/W/O emulsion in a water phase to obtain an S/W/O/W emulsion; and removing the organic solvent from the S/W/O/W emulsion, a method for producing a microcapsule formulation using a biodegradable polymer can be provided, the method being capable of avoiding denaturation of a physiologically active substance even when the physiologically active substance is in direct exposure to an oil-water interface and achieving a high encapsulation efficiency for the physiologically active substance, etc.

The term "heavy metal salt of a peptidic physiologically active substance" as used herein refers to a precipitate or aggregate that is insoluble in both water and organic solvents and that is obtained by mixing a peptidic physiologically active substance and a heavy metal salt, unless otherwise specified.

The present invention has been accomplished with further research based on this finding. Specifically, the present invention provides the following methods for producing a microcapsule formulation containing a peptidic physiologically active substance.

Item 1. A method for producing a microcapsule formulation comprising:
  step A of adding a basic amino acid to an aqueous solvent containing a heavy metal salt of a peptidic physiologically active substance to obtain an amino acid-containing S/W suspension;
  step B of adding a basic amino acid to an organic solvent containing a biodegradable polymer to obtain an amino acid-containing polymer solution;
  step C of dispersing the amino acid-containing S/W suspension in the amino acid-containing polymer solution, which is an oil phase, to obtain an S/W/O emulsion;
  step D of dispersing the S/W/O emulsion in a water phase to obtain an S/W/O/W emulsion; and
  step E of removing the organic solvent from the S/W/O/W emulsion to obtain the microcapsule formulation.

Item 2. The method according to Item 1, wherein the molar ratio of the basic amino acid contained in the amino acid-containing S/W suspension to the basic amino acid contained in the amino acid-containing polymer solution (the basic amino acid content of the amino acid-containing S/W suspension to the basic amino acid content of the amino acid-containing polymer solution) is 1:5 to 5:1.

Item 3 The method according to Item 1 or 2, wherein the heavy metal salt of the peptidic physiologically active substance has a mean particle size of 1 μm or less and is insoluble in both water and organic solvents.

Item 4 The method according to any one of Items 1 to 3, further comprising adding a heavy metal salt to an aqueous solvent containing a peptidic physiologically active substance to obtain the aqueous solvent containing a heavy metal salt of the peptidic physiologically active substance.

Item 5 The method according to any one of Items 1 to 4, wherein the peptidic physiologically active substance has an IgG structure.

Item 6 The method according to any one of Items 1 to 5, wherein the peptidic physiologically active substance is TuNEX.

Item 7 The method according to any one of Items 1 to 6, wherein the heavy metal salt is a zinc salt.

Item 8 The method according to any one of Items 1 to 7, wherein the basic amino acid is L-arginine or L-histidine.

Item 9 The method according to any one of Items 1 to 8, further comprising step F of subjecting microcapsules obtained by removing the organic solvent from the S/W/O/W emulsion in step E to freeze-drying or spray-drying to form a powder.

Item 10 The method according to any one of Items 1 to 9, wherein the biodegradable polymer is a polylactic acid, a lactic acid-glycolic acid copolymer, or a mixture thereof.

Item 11 The method according to Item 10, wherein the molar ratio of lactic acid to glycolic acid (lactic acid:glycolic acid) in the biodegradable polymer is 99:1 to 50:50.

Item 12 The method according to Item 11, wherein the molar ratio of lactic acid to glycolic acid (lactic acid:glycolic acid) in the biodegradable polymer is 75:25 to 50:50.

Item 13 The method according to any one of Items 1 to 12, wherein the biodegradable polymer has a weight average molecular weight of 3,000 to 200,000.

Item 14 The method according to Item 13, wherein the biodegradable polymer has a weight average molecular weight of 3,000 to 50,000.

Item 15 The method according to Item 14, wherein the biodegradable polymer has a weight average molecular weight of 5,000 to 20,000.

Item 16 A microcapsule formulation produced by the method according to any one of Items 1 to 15.

Advantageous Effects of Invention

According to the present invention, a production method that can avoid direct contact of a peptidic physiologically active substance with an organic solvent layer can be provided. A production method that achieves a high encapsulation efficiency for a peptidic physiologically active substance can be provided.

DESCRIPTION OF EMBODIMENTS

Figure 1:
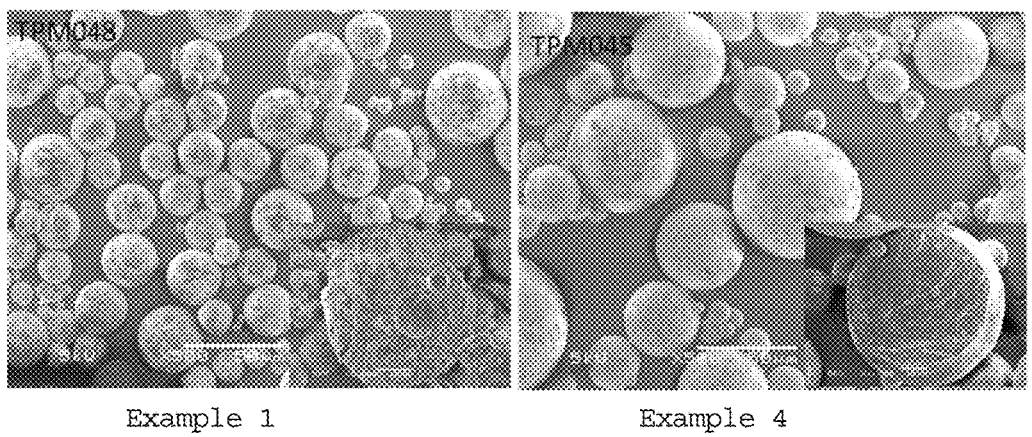
FIG. 1 shows scanning electron micrographs (SEM) of the surface and cross-section of microcapsules obtained in Examples 1 and 4.
Figure 2:
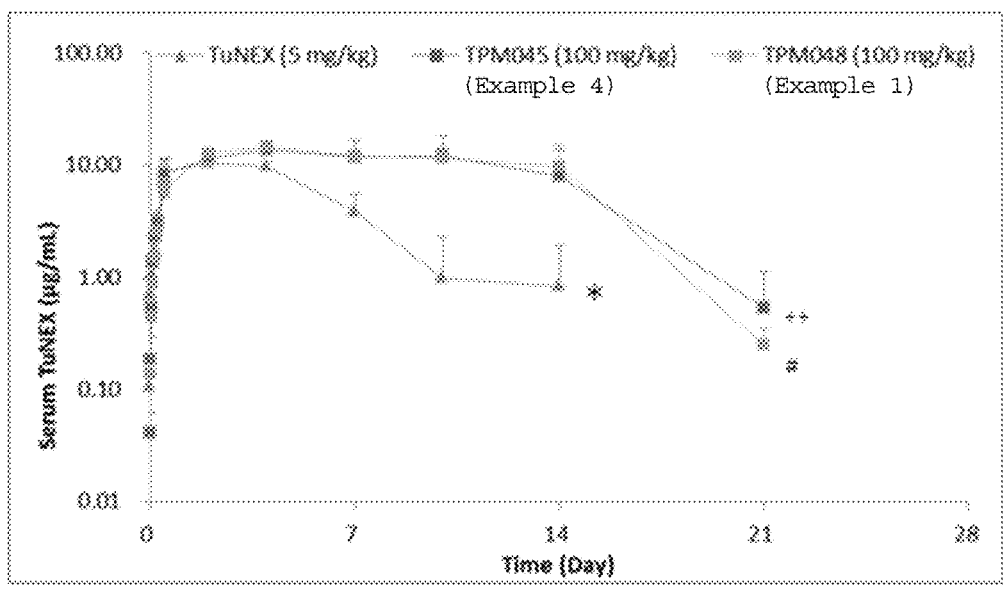
FIG. 2 is a graph showing the serum drug concentration profiles after subcutaneous administration of the microcapsules of Examples 1 and 4 to rats.

The present invention is described in detail below.

In this specification, "room temperature" refers to a temperature in the range of 1 to 30° C. unless otherwise specified.

Method for Producing the Microcapsule Formulation

The method for producing the microcapsule formulation of the present invention comprises:
  step A of adding a basic amino acid to an aqueous solvent containing a heavy metal salt of a peptidic physiologically active substance to obtain an amino acid-containing S/W suspension;
  step B of adding a basic amino acid to a biodegradable polymer-containing organic solvent to obtain an amino acid-containing polymer solution;
  step C of dispersing the amino acid-containing S/W suspension in the amino acid-containing polymer solution, which is an oil phase, to obtain an S/W/O emulsion;
  step D of dispersing the S/W/O emulsion in a water phase to obtain an S/W/O/W emulsion; and
  step E of removing the organic solvent from the S/W/O/W emulsion. Each of steps A to E is explained below.

Step A

In step A, a basic amino acid is added to an aqueous solvent containing a heavy metal salt of a peptidic physiologically active substance (hereinafter sometimes referred to as a "peptide salt") to obtain an amino acid-containing S/W suspension.

Examples of peptidic physiologically active substances include compounds that comprise a peptide consisting of amino acid residues and that can exhibit physiological activity useful in vivo. There is no particular limitation on the molecular weight. Even peptidic physiologically active substances that have a molecular weight of more than 150,000 can be suitably used. Specific examples of peptidic physiologically active substances include hormones, cytokines, hematopoietic factors, growth factors, enzymes, soluble or solubilized receptors, antibodies, partial regions constituting antibodies, peptidic antigens, blood coagulation factors, adhesion factors, and substances obtained by binding these to the constant region of an antibody. In one embodiment, the peptidic physiologically active substance may be a serum albumin (such as human serum albumin (HSA)).

Examples of hormones include insulin, growth hormone, natriuretic peptides, gastrin, prolactin, adrenocorticotropic hormone (ACTH), thyroid-stimulating hormone (TSH), lutenizing hormone (LH), follicle-stimulating hormone (FSH), human chorionic gonadotropin (HCG), motilin, and kallikrein.

Examples of cytokines include lymphokine and monokine. Examples of lymphokines include interferons (alpha, beta, gamma), and interleukins (one or more of IL-2 through IL-12). Examples of monokines include interleukin 1 (IL-1) and tumor necrosis factors.

Examples of hematopoietic factors include erythropoietin, granulocyte colony-stimulating factors (G-CSF), macrophage colony-stimulating factors (M-CSF), thrombopoietins, platelet growth-stimulating factors, and megakaryocyte potentiators.

Examples of growth factors include basic or acidic fibroblast growth factors (FGF) or families thereof (e.g., FGF-9); nerve cell growth factors (NGF) or families thereof; insulin-like growth factors (e.g., IGF-1 and IGF-2), bone morphogenetic protein (BMP), hepatocyte growth factor (HGF), or families thereof.

Examples of enzymes include superoxide dismutase (SOD) and tissue plasminogen activator (tPA).

Examples of soluble receptors include soluble interleukin 6 (IL-6) receptor, insulin-like growth factor binding protein (IGFBP), soluble tumor necrosis factor receptors, soluble epidermal growth factor receptors, and soluble interleukin 1 receptors.

Examples of solubilized receptors include those obtained by solubilizing known receptors, such as interleukin 1 receptor, interleukin-6 receptor, tumor necrosis factor receptors, and Fas ligand, by genetic engineering techniques.

Examples of antibodies include human monoclonal antibodies, and human-mouse chimeric monoclonal antibodies comprising a mouse-derived variable region and a human-derived constant region. The types of antibodies include IgM, IgG, and IgE. Examples of antigens include those recognized by the above-mentioned antibodies, and also include platelets and viruses. Other examples of antibodies include substances obtained by binding an antibody to a cell, and substances obtained by binding an antibody to other compounds.

Examples of blood coagulation factors include factor VIII.

Examples of adhesion factors include fibronectin and ICAM-1.

Examples of physiologically active substances include endothelin, Arg-Gly-Asp-Ser (RGDS), and pituitary adenylate cyclase activating polypeptide (PACAP).

Among the above peptidic physiologically active substances, Etanercept, or TuNEX, which is a recombinant TNF-α receptor protein and which is an antibody having an amino acid sequence similar to that of etanercept and having a molecular weight of about 150,000, can be mentioned as an example using an IgG antibody. Etanercept and TuNEX have a short half-life in vivo and are one of the peptidic physiologically active substances for which the development of sustained release formulations has been particularly strongly desired (NPL 6).

Only one, or two or more of the peptidic physiologically active substances mentioned above may be used as the peptidic physiologically active substance.

Examples of the heavy metal that forms a peptide salt include bivalent, trivalent, or tetravalent metals. Specific examples include alkaline earth metals, such as calcium and magnesium; transition metals, such as iron, copper, and zinc; aluminum, and tin. Among these, alkaline earth metals or transition metals are preferable, and zinc is particularly preferable.

The basic amino acid is not particularly limited, and examples include arginine, lysine, and histidine. The basic amino acid may be either D-amino acid or L-amino acid. A mixture of D-amino acid and L-amino acid may be used. Among these, L-arginine or L-histidine is preferable, and L-arginine is particularly preferable. The S/w suspension obtained in step A may contain only one, or two or more, of these basic amino acids. The basic amino acid must be a free amino acid, not in the form of a salt.

The aqueous solvent containing a peptide salt is obtained by adding a heavy metal salt (hereinafter sometimes referred to as a "heavy metal salt for addition") to an aqueous solution containing a peptidic physiologically active substance and mixing.

Examples of the method for producing the peptide salt include the following method. However, usable methods are not limited thereto.

First, an aqueous solution containing a peptidic physiologically active substance is mixed with a heavy metal salt for addition while stirring to precipitate a heavy metal salt of the peptidic physiologically active substance. The precipitate is separated by centrifugation. The conditions for centrifugation are not particularly limited. For example, the centrifugation can be performed at 4° C. at 7,400 rpm for 10 minutes.

It is usually preferable that the concentration of the peptidic physiologically active substance in the aqueous solution containing a peptidic physiologically active substance be 5 w/v % or less.

The molar ratio of the heavy metal salt for addition to the peptidic physiologically active substance (heavy metal salt for addition/peptidic physiologically active substance) is not particularly limited, and may be any ratio within the range of 1,000 or less. The lower limit is preferably 10, and more preferably 30. The upper limit is preferably 650, more preferably 400, and particularly preferably 100. When the lower limit is 10, the upper limit is preferably 650, more preferably 400, and particularly preferably 100. When the lower limit is 30, the upper limit is preferably 650, more preferably 400, and particularly preferably 100.

The obtained peptide salt is preferably freeze-dried into a powder. This can enhance its long-term chemical stability.

Subsequently, the obtained peptide salt is dispersed in an aqueous solvent. A basic amino acid is added to the dispersion of the peptide salt in the aqueous solvent, and mixed to obtain an amino acid-containing S/W suspension to be subjected to step B below.

The heavy metal salt for addition can be added in the form of an aqueous solution containing the heavy metal salt for addition. The concentration of the heavy metal salt in the aqueous solution containing the heavy metal salt for addition varies depending on the type of peptidic physiologically active substance. The lower limit may be 0.01 w/v %. The upper limit may be 1 w/v %, and preferably 0.5 w/v %. That is, the concentration of the heavy metal salt may be in the range of 0.01 to 1 w/v %, and preferably 0.01 to 0.5 w/v %.

The heavy metal salt for addition is not particularly limited, and examples include heavy metal salts with organic acids and heavy metal salts with inorganic acids. The salts with inorganic acids are preferable.

Examples of the salts with inorganic acids include halogenated salts (e.g., zinc chloride and calcium chloride), sulfates, nitrates, and thiocyanates. Zinc chloride is particularly preferable.

Examples of organic acids in the salts with organic acids include aliphatic carboxylic acids and aromatic acids. The aliphatic carboxylic acids are preferably aliphatic carboxylic acids having 2 to 9 carbon atoms. Examples of aliphatic carboxylic acids include aliphatic monocarboxylic acids, aliphatic dicarboxylic acids, and aliphatic tricarboxylic acids. These aliphatic carboxylic acids may be saturated or unsaturated.

The content of the peptidic physiologically active substance in the peptide salt is preferably in the range of 1 to 30 w/w %, based on the amount of the peptide salt being set to 100 w/w/%.

The particle size of the peptide salt is preferably 1 μm or less. Finer particles are preferable. The particle size is not particularly limited. The lower limit may be 100 nm. The upper limit is preferably 600 nm.

Either or both of the aqueous solution containing a peptidic physiologically active substance and the aqueous solution containing a heavy metal salt for addition may contain other additives. Examples of such additives include polyvinyl alcohol (PVA) and Polysorbate 80. Among these, PVA is preferable. Incorporation of such an additive can reduce the particle size of the peptide salt in the aqueous solvent containing the peptide salt. Reduction of the particle size of the peptide salt enables the production of a microcapsule formulation of the present invention in which a peptidic physiologically active substance is more uniformly dispersed.

When PVA is added to either the aqueous solution containing a peptidic physiologically active substance or the aqueous solution containing a heavy metal salt for addition, the concentration of PVA is not particularly limited and may be 0.05 to 2 w/v %.

The molar ratio of the heavy metal salt for addition to the peptidic physiologically active substance (the heavy metal salt for addition/peptidic physiologically active substance) is not particularly limited, and is preferably 10 to 1,250.

Examples of the method for dispersing the peptide salt in an aqueous solvent include an intermittent shaking method, methods using a mixer, such as a propeller agitator or a turbine agitator, a colloidal mill method, a homogenizer method, and an ultrasonication method.

The aqueous solvent may be any aqueous solvent other than aqueous solvents (e.g., physiological saline) that are capable of dissolving the peptide salt. Examples include water and pH buffers.

When the peptide salt is dispersed in an aqueous solvent, the aqueous solvent containing the peptide salt is preferably subjected to ultrasonic irradiation. The ultrasonic irradiation can reduce the particle size of the obtained peptide salt. The conditions for ultrasonic irradiation are not particularly limited. For example, 20-second irradiation can be repeated with intervals of 5 seconds for 20 minutes. Specifically, the irradiation can be performed at a frequency of 20 kHz for a total ultrasonic irradiation time of 16 minutes.

When a basic amino acid is added to and mixed with an aqueous solvent in which the peptide salt is dispersed, the aqueous solvent may be heated as long as the activity of the peptidic physiologically active substance and the effect of the present invention are not impaired. Heating can reduce the viscosity of the aqueous solvent and increase the solubility of the basic amino acid, thus providing an amino acid-containing S/W suspension in which a peptidic physiologically active substance or the like is more uniformly dispersed.

In place of or in addition to heating, ultrasonic irradiation within the range that the activity of the peptidic physiologically active substance and the effect of the present invention are not impaired is also effective for more uniformly dispersing the peptide physiologically active substance, etc.

Because more uniform dispersion of the peptidic physiologically active substance in the microcapsule formulation contributes to the release of the peptidic physiologically active substance at a constant rate, addition and mixing of a basic amino acid while heating or under ultrasonic irradiation is considered to be highly useful.

The lower limit of the heating temperature may be 25° C., and preferably 30° C., and more preferably 35° C. The upper limit of the heating temperature may be 45° C., and preferably 40° C. When the lower limit is 25° C., the upper limit may be 45° C., and preferably 40° C. When the lower limit is 30° C., the upper limit may be 45° C., and preferably 40° C. When the lower limit is 35° C., the upper limit may be 45° C., and preferably 40° C. When the heating temperature is within the above-mentioned range, a more uniform amino acid-containing S/W suspension can be prepared while maintaining the activity of the peptidic physiologically active substance.

The peptide salt is insoluble in both water and organic solvents but dissolves in physiological saline. The peptidic physiologically active substance eluted by dissolving the peptide salt can exhibit physiological activity equivalent to that of the peptidic physiologically active substance before being formed into the peptide salt. Specifically, when the peptide salt is administered in vivo, the peptide salt dissolves in vivo and the eluted peptidic physiologically active substance can exhibit the desired physiological activity.

Step B

In step B, a basic amino acid is added to an organic solvent containing a biodegradable polymer to obtain an amino acid-containing polymer solution.

Any biodegradable polymer that gradually degrades in vivo to exhibit the desired sustained-release performance may be used. For example, aliphatic polyesters, poly-α-cyanoacrylic acid esters, and polyamino acids can be used. Aliphatic polyesters are preferable. Such polymers may be mixed at a suitable ratio. The form of polymerization may be any of random, block, or graft polymerization. Random polymerization is the most preferable.

Specific examples of biodegradable polymers include polylactic acid, polyglycolic acid, lactic acid-glycolic acid copolymer (PLGA), polycitric acid, polymalic acid, lactic acid-aspartic acid copolymer, lactic acid-hydroxycaproic acid copolymer, glycolic acid-hydroxycaproic acid copolymer, polypropiolactone, polybutyrolactone, polyvalerolactone, polycaprolactone, polytrimethylene carbonate, poly(p-dioxanone), poly(a-cyanoacrylic acid ester), poly(β-hydroxybutyric acid), polytrimethylene oxalate, polyorthoester, polyorthocarbonate, polyethylene carbonate, poly-γ-benzyl-L-glutamic acid, poly-L-alanine, polyalginic acid, polycarbonate, polyester amide, polyamino acid, polyalkylene alkylate, polyethylene glycol, polyurethane, and like homopolymers, and copolymers thereof. Among these, polylactic acid and lactic acid-glycolic acid copolymers (PLGA) are preferable. Such biodegradable polymers may be used singly or as a mixture of two or more.

When a polylactic acid or lactic acid-glycolic acid copolymer (PLGA) is used, its molecular weight can be suitably selected from a wide range. For example, the polylactic acid or lactic acid-glycolic acid copolymer (PLGA) may have a molecular weight of about 3,000 to 200,000, preferably about 3,000 to 50,000, and more preferably about 5,000 to 20,000.

The ratio of lactic acid to glycolic acid (lactic acid:glycolic acid in the lactic acid-glycolic acid copolymer is not particularly limited, and can be suitably selected from a wide range. The lactic acid:glycolic acid molar ratio is typically in the range of about 99:1 to 50:50, and preferably about 75:25 to 50:50.

The polylactic acid may be any of poly-D-lactic acid, poly-L-lactic acid, and poly-DL-lactic acid. Poly-DL-lactic acid is preferable. The lactic acid-glycolic acid copolymer (PLGA) may be any of a D-lactic acid-glycolic acid copolymer, an L-lactic acid-glycolic acid copolymer, and a DL-lactic acid-glycolic acid copolymer. A DL-lactic acid-glycolic acid copolymer is preferable.

The biodegradable polymer preferably has a free carboxyl group at an end. The free carboxyl group probably allows the biodegradable polymer to exhibit a surfactant activity on the interface between the amino acid-containing S/W suspension and the amino acid-containing polymer solution in step C described below, thus providing a more stable S/W/O emulsion.

The concentration of the biodegradable polymer is not particularly limited. The lower limit may be 5 w/v %, preferably 20 w/v %, and more preferably 40 w/v %. The upper limit may be 30 w/v %, preferably 40 w/v %, and more preferably 60 w/v %. When the lower limit is 5 w/v %, the upper limit may be 30 w/v %, preferably 40 w/v %, and more preferably 60 w/v %. When the lower limit is 20 w/v %, the upper limit may be 30 w/v %, preferably 40 w/v %, and more preferably 60 w/v %. When the lower limit is 40 w/v %, the upper limit may be preferably 60 w/v %.

The organic solvent is not particularly limited, as long as it can dissolve biodegradable polymers. Examples of such organic solvents include halogenated hydrocarbons, such as chloroform, dichloroethane, trichloroethane, dichloromethane, and carbon tetrachloride; ethers, such as ethyl ether and isopropyl ether; fatty acid esters such as ethyl acetate and butyl acetate; aromatic hydrocarbons, such as benzene, toluene, and xylene; alcohols, such as ethanol, methanol, and isopropanol; nitriles, such as acetonitrile; amides, such as dimethylformamide; and acetones, such as dimethyl ketone and methyl ethyl ketone. Among these, water-immiscible organic solvents are preferable. Dichloromethane is particularly preferable. Such organic solvents may be used alone or as a mixture of two or more. Ethers and alcohols are preferably used as a mixed solvent of two or more.

Only one, or two or more of the basic amino acids mentioned above may be used as the basic amino acid. The basic amino acid used in step B may be different from the basic amino acid used in step A, but the same basic amino acid is preferably used.

The organic solvent containing a biodegradable polymer can be obtained, for example, by adding a biodegradable polymer to an organic solvent and stirring. Ultrasonic irradiation within the range that the effect of the present invention is not impaired may facilitate dissolution of the biodegradable polymer.

The amino acid-containing polymer solution can be prepared, for example, by adding a basic amino acid to the organic solvent containing a biodegradable polymer and dissolving the amino acid therein.

When a basic amino acid is dissolved, adding the basic amino acid to an organic solvent containing a biodegradable polymer and leaving the mixture at room temperature overnight can also facilitate the dissolution of the biodegradable polymer and the basic amino acid. Dissolving the basic amino acid over such a long period of time is effective for obtaining an amino acid-containing polymer solution in which both the biodegradable polymer and the basic amino acid are uniformly dissolved. Ultrasonic irradiation after leaving the mixture overnight is also effective for obtaining a uniform solution as mentioned above. The conditions for ultrasonic irradiation are not particularly limited. For example, 20-second irradiation can be repeated with intervals of 5 seconds for 20 minutes. Specifically, the irradiation can be performed at a frequency of 20 kHz for a total ultrasonic irradiation time of 16 minutes.

Step C

In step C, the amino acid-containing S/W suspension is dispersed in the amino acid-containing polymer solution, which is an oil phase, to obtain an S/W/O emulsion.

When the organic solvent in the amino acid-containing polymer solution is a water-immiscible solvent, the amino acid-containing S/W suspension is dispersed in the form of small droplets in the amino acid-containing polymer solution.

The method for dispersion includes, for example, an intermittent shaking method, a method using a mixer, such as a propeller agitator or a turbine agitator, a colloidal mill method, a homogenizer method, and an ultrasonication method.

The method for preparing the S/W/O emulsion is not particularly limited. Examples of usable methods include a method of producing an S/W/O emulsion comprising stirring a mixture of an amino acid-containing S/W suspension and an amino acid-containing polymer solution using a homogenizer or the like at a suitable rotational speed to form the S/W dispersion into finely divided particles in an aqueous solvent; a method of producing an S/W/O emulsion comprising passing a mixture of an amino acid-containing S/W suspension and an amino acid-containing polymer solution through a filter with small through-pores, such as a ceramic filter, at a constant rate to form the emulsion containing finely divided particles, and a method comprising passing an amino acid-containing S/W suspension through a filter with small through-pores, such as a ceramic filter, at a constant rate to form the suspension into finely divided particles and then mixing the finely divided suspension particles with an amino acid-containing polymer solution.

Specific examples of the method for preparing the S/W/O emulsion include the following method. However, usable methods are not limited thereto.

First, the amino acid-containing S/W suspension is slowly added dropwise to the amino acid-containing polymer solution.

The amino acid-containing polymer solution to which the amino acid-containing S/W suspension has been added is stirred at 9,600 rpm using a homogenizer to obtain an S/W/O emulsion.

The mixing ratio of the amino acid-containing S/W suspension to the amino acid-containing polymer solution is not particularly limited, as long as a S/W/O emulsion is obtained. The mixing ratio by volume is preferably in the range of 1:3 to 1:30, and more preferably 1:5 to 1:20.

The basic amino acid content of the S/W/O emulsion is preferably 1 to 10 w/w %, more preferably 1 to 8 w/w %, and even more preferably 2 to 6 w/w %, relative to the biodegradable polymer.

In step C, ultrasonic irradiation of the amino acid-containing S/W suspension and the amino acid-containing polymer solution within the range that the activity of the peptidic physiologically active substance and the effect of the invention are not impaired is effective for more uniformly dispersing the peptidic physiologically active substance. Ultrasonic irradiation can reduce the particle size of the droplets in the S/W/O emulsion obtained in step C, so that the amino acid-containing S/W suspension can be more uniformly and easily dispersed in the amino acid-containing polymer solution.

Because more uniform dispersion of the peptidic physiologically active substance in a microcapsule formulation contributes to the release of the peptidic physiologically active substance at a constant rate, performing step C while heating and/or under ultrasonic irradiation is considered to be highly useful.

In the production method of the present invention, both the amino acid-containing S/W suspension and the amino acid-containing polymer solution contain a basic amino acid.

The basic amino acid distribution ratio in the amino acid-containing S/W suspension and the amino acid-containing polymer solution, as a molar ratio (the basic amino acid contained in the amino acid-containing S/W suspension:the basic amino acid contained in the amino acid-containing polymer solution), is in the range of 1:5 to 5:1, preferably 1:3 to 3:1, and particularly preferably 1:1.

When arginine is used as the basic amino acid, the concentration of the basic amino acid in the amino acid-containing S/W suspension may be, for example, 0.05 to 0.075 w/v %, and the concentration of the basic amino acid in the amino acid-containing polymer solution may be, for example, 0.01 to 0.03 w/v %. The lower limit of the basic amino acid in the S/W/O emulsion obtained in step C may be 0.01 w/v %, preferably 0.03 w/v %, and more preferably 0.05 w/v %. The upper limit may be 0.1 w/v %, preferably 0.5 w/v %, and more preferably 1 w/v %. When the lower limit is 0.01 w/v %, the upper limit may be 0.1 w/v %, preferably 0.5 w/v %, and more preferably 1 w/v %. When the lower limit is 0.03 w/v %, the upper limit may be 1 w/v %, preferably 0.5 w/v %, and more preferably 1 w/v %. When the lower limit is 0.05 w/v %, the upper limit may be 0.1 w/v %, preferably 0.5 w/v %, and more preferably 1 w/v %.

When PLGA is used as the biodegradable polymer, the molar ratio of the basic amino acid contained in the S/W/O emulsion to PLGA calculated from the number average molecular weight (basic amino acid:PLGA) is preferably in the range of 2:1 to 1:5, and more preferably 2:1 to 1:2.

Setting the basic amino acid distribution ratio to the above-mentioned range can provide a surprising effect, i.e., remarkably enhance the encapsulation efficiency of the peptidic physiologically active substance in the S/W/O/W emulsion.

Step D

In Step D, the S/W/O emulsion is dispersed in a water phase to obtain an S/W/O/W emulsion.

The water phase is not particularly limited, and any aqueous solvent can be used. Water is preferable.

The water phase may contain an emulsifier. A preferable emulsifier may be any emulsifier that can form a stable S/W/O/W emulsion. Examples of such emulsifiers include anionic surfactants, such as sodium oleate, sodium stearate, and sodium lauryl sulfate; nonionic surfactants, such as polyoxyethylene sorbitan fatty acid esters and polyoxyethylene castor oil derivatives; polyvinylpyrrolidones, polyvinyl alcohol (PVA), carboxymethyl cellulose, lecithin, gelatin, and hyaluronic acid. Such emulsifiers may be used singly or in a combination of two or more.

When the water phase contains an emulsifier, the concentration of the emulsifier is not particularly limited and may vary according to the type of emulsifier. The concentration is preferably the critical micelle concentration or higher. When a nonionic surfactant is used as the emulsifier, its concentration may be, for example, about 0.005 to 0.5 w/v %, preferably about 0.01 to 0.1 w/v %, and more preferably about 0.01 to 0.05 w/v %, based on the amount of the water phase. When PVA is used as the emulsifier, its concentration may be, for example, about 0.01 to 0.5 w/v %, preferably about 0.01 to 0.1 w/v %, and more preferably about 0.05 to 0.1 w/v %, based on the amount of the water phase.

The method for preparing the S/W/O/W emulsion is not particularly limited. Examples of usable methods include a method comprising stirring a mixture of an S/W/O emulsion and an aqueous solvent, which is a water phase, at a suitable rotational speed using a homogenizer or the like to form the S/W/O emulsion into finely divided particles in the aqueous solvent, thus obtaining an S/W/O/W emulsion, a method comprising passing a mixture of an S/W/O emulsion and an aqueous solvent, which is a water phase, through a filter with small through-pores, such as a ceramic filter, at a constant rate to form the emulsion containing finely divided particles, thus obtaining an S/W/O/W emulsion, a method comprising passing an S/W/O emulsion through a filter with small through-pores, such as a ceramic filter, at a constant rate to form the emulsion into finely divided particles and then mixing the emulsion with an aqueous solvent, which is a water phase. During the formulation of the emulsion, the water phase preferably has a temperature of 20° C. or lower, and more preferably 15° C. or lower.

Specific examples of the method for preparing the S/W/O/W emulsion include the following method. However, usable methods are not limited thereto.

First, the temperature of the water phase is adjusted to 15° C. or lower. While stirring the water phase using a homogenizer, an S/W/O suspension is slowly added dropwise to the aqueous solvent from exactly above the rotor. The water phase containing the S/W/O suspension is further stirred gently to obtain an S/W/O/W emulsion.

The amount of the water phase for dispersing the S/W/O suspension is not particularly limited as long as an S/W/O/W emulsion is obtained. Any amount that is in an excess relative to the amount of the S/W/O emulsion may be used.

For example, at least 5 equivalents of the water phase is preferable, and at least 10 equivalents is more preferable.

Step E

In step E, the organic solvent in the S/W/O/W emulsion obtained in step D is removed to obtain a microcapsule formulation.

As the method for removing the organic solvent in step E, an in-water drying method or the like that is usually used may be used. Examples of usable methods include a method of stirring using a paddle mixer or a magnetic stirrer, a method of gradually reducing pressure while stirring with a paddle mixer or a magnetic stirrer, or a method of adjusting the vacuum using a rotary evaporator or the like. In this step, the S/W/O/W emulsion may have room temperature, preferably has a temperature of 20° C. or lower, and more preferably 15° C. or lower.

Specific examples of the method for removing the organic solvent from the S/W/O/W emulsion include the following method. However, usable methods are not limited thereto.

An S/W/O/W emulsion was stirred at 650 rpm using a paddle mixer at room temperature for 3 hours.

In Step E, the organic solvent was removed from the S/W/O/W emulsion to form a microcapsule having a peptidic physiologically active substance dispersed therein.

Step F

The production method of the present invention may further comprise step F.

In step F, the microcapsules are washed, and then freeze-dried or spray-dried into a powder.

The microcapsules formed in step E can be collected by a method such as centrifugation. The collected microcapsules can be washed with water.

The freeze-drying conditions and spray-drying conditions for microcapsules can be suitably set. The powder obtained by freeze-drying or spray-drying the microcapsules can be formed into a microcapsule formulation in the form of an injection that is more suitable for administration by adding distilled water for injection, physiological saline for injection, and other appropriate dispersants, when used.

Microcapsule Formulation

According to the production method of the present invention, a production method that can stably retain a peptidic physiologically active substance and that can achieve a high encapsulation efficiency of the peptidic physiologically active substance is provided. Furthermore, the microcapsule formulation obtained by the production method of the present invention comprises a peptidic physiologically active substance highly uniformly dispersed therein. Specifically, the obtained microcapsule formulation is considered to have a structure such that a fine peptide salt is uniformly dispersed in a matrix of a biodegradable polymer, and a basic amino acid is interposed at the interface between the peptide salt and the matrix of the biodegradable polymer.

In one preferable embodiment of the invention, a microcapsule formulation that can release a peptidic physiologically active substance at an almost constant rate can be obtained.

Measurement Method

Method for Extracting a Peptidic Physiologically Active Substance from a Microcapsule Formulation 5 to 10 mg of a microcapsule formulation is dispersed in 1 mL of acetone. The dispersion is sonicated in an ice bath for 20 minutes. The obtained liquid is added to 9 mL of a 0.9 w/v % aqueous sodium chloride solution and mixed. The mixture is sonicated in an ice bath for 20 minutes. The resulting liquid is centrifuged to remove the precipitate. The obtained liquid is assayed by the micro BCA protein assay and ELISA assay described below.

When a peptidic physiologically active substance is extracted from a peptide salt, the peptide salt is added to a 0.9 w/v % aqueous sodium chloride solution and mixed. The obtained liquid is sonicated in an ice bath for 20 minutes. The resulting liquid is centrifuged to remove the precipitate. The obtained liquid is assayed by the micro BCA protein assay and ELISA assay described below.

Physiologically Active Substance Content

Measurement method: Micro BCA (Bicinchoninic Acid) protein assay

Measurement conditions: Micro BCA Protein Assay Reagent A, Reagent B, and Reagent C are mixed at an A:B:C ratio of 25:24:1. Five dilutions of a TuNEX standard in the range of 2 to 50 μg/mL are prepared. 150 μL of the standard or a sample is pipetted into each well of a 96-well microplate, and 150 μL of a dye reagent is added thereto and mixed. After incubation at 37° C. for 2 hours, absorbance is measured at 570 nm using a plate reader. Based on the calibration curve obtained from the absorbance of the standard, the protein mass is calculated.

Binding Activity

Measurement method: ELISA Assay

Measurement apparatus: Thermo Scientific Multiskan Ascent (a plate reader manufactured by Thermo Labsystems Inc.)

Measurement conditions: A mouse anti-human TNF RII/TNFRSF1B monoclonal antibody is coated on each well of a 96-well microplate. A standard solution is prepared by adding TuNEX (100 μ/mL) to 1% bovine serum albumin phosphate buffered saline (BSA-PBS). 100 μL of the standard solution or a sample is pipetted into each well. An anti-human IgG Fc-HRP is added to 1% BSA-PBS, and 100 μL of this liquid is pipetted into each well, followed by incubation at 37° C. for 1 hour. After washing each well, 100 μL of an ortho-phenyldiamine (OPD) solution is pipetted into each well, and the mixture is incubated at 37° C. for 10 minutes while gently stirring. 50 μL of a $H_2SO_4$ solution is pipetted into each well to stop the enzymatic reaction. The absorbance is measured at a wavelength of 490 nm using a microplate reader. The binding activity is calculated from the obtained sigmoid curve.

Measurement of the Mean Particle Size

Measurement apparatus: Beckmann Coulter Multisizer III (manufactured by Beckmann Instruments Inc.)

Measurement conditions: An appropriate amount of the sample is dispersed in physiological saline. The mean particle size is measured by the resistive pulse method (electronic sensing zone method).

Encapsulation Efficiency (EE)

Calculation method: The TuNEX encapsulation efficiency is calculated using the equations below.

Specifically, the drug loading amount is calculated using the following equation 1:

$$DL[mg] = Mmc[mg] \times \frac{Mt[mg]}{Mp[mg] + Mtz[mg] + Mar[mg]} \quad \text{[Equation 1]}$$

(wherein DL: initial drug loading amount (mg), Mmc: weight of the microcapsule including zinc salt of TuNEX and PLGA (mg), Mt: weight of TuNEX (mg), Mp: weight of PLGA (mg), Mtz: weight of zinc salt of TuNEX (mg), and Mar: weight of basic amino acid (mg).) The encapsulation efficiency is calculated from this value using the following equation 2:

$$EE[\%] = \frac{Md[mg]}{DL[mg]} \times 100 \quad \text{[Equation 2]}$$

(wherein EE: encapsulation efficiency (%), Md: drug amount determined by the micro BCA protein assay (mg), and DL: initial drug loading amount (mg)).

EXAMPLES

The present invention is described below in more detail with reference to Examples. However, the present invention is not limited thereto or thereby.

Various evaluation parameters used in the Examples were determined by the measurement methods described above.

Example 1 TPM048

20 mL of TuNEX (3.5 mg/mL) was mixed with 4 mL of an aqueous zinc chloride solution (1.0 mg/mL) to obtain a zinc salt of TuNEX. This liquid was centrifuged to separate the zinc salt. The zinc salt was washed with water and freeze-dried. 550 mg of the freeze-dried zinc salt was dispersed in 1.1 mL of water to obtain an aqueous solvent containing the zinc salt. The zinc salt had a mean particle size of about 170 nm.

71.8 mg of L-arginine (produced by Sigma-Aldrich, Inc.) was added to the aqueous solvent containing the zinc salt. The resulting mixture was heated to 40° C. and sonicated to dissolve L-arginine, thus obtaining an amino acid-containing S/W suspension. Separate from this, 2,750 mg of a lactic acid-glycolic acid copolymer (PLGA) (produced by Wako Pure Chemical Industries, Ltd., weight average molecular weight: about 10,000, lactic acid:glycolic acid ratio=50:50, containing free carboxyl groups) was dissolved in 5.5 mL of dichloromethane (DCM), and 71.8 mg of L-arginine (produced by Sigma-Aldrich, Inc.) was added. The resulting mixture was allowed to stand overnight to dissolve L-arginine, thus obtaining an amino acid-containing polymer solution. Subsequently, the S/W suspension was added to the polymer solution, and stirred at scale 6 with a homogenizer (Homogenizer T10) for 1 minute to obtain an S/W/O emulsion. Subsequently, the S/W/O emulsion was added to 330 mL of an aqueous solution containing 0.1 w/v % of polyvinyl alcohol (PVA), which is a water phase, and the mixture was stirred at 18,000 rpm for 3 minutes using a homogenizer (Homogenizer T10) to obtain an S/W/O/W emulsion. The S/W/O/W emulsion was slowly stirred at 650 rpm using a paddle mixer at room temperature for 3 hours to distill off dichloromethane, and centrifuged at 6,000 rpm for 2 minutes to collect microcapsules. The microcapsules were washed with water and then freeze-dried to form a powdery microcapsule formulation.

Example 2 TPM051R

A microcapsule formulation was produced in the same manner as in Example 1 except that 35.9 mg of L-arginine (produced by Sigma-Aldrich, Inc.) was added to the aqueous solvent containing a zinc salt, and 107.7 mg of L-arginine (produced by Sigma-Aldrich, Inc.) was added to the solution of PLGA in DCM.

Example 3 TPM052R

A microcapsule formulation was produced in the same manner as in Example 1 except that 107.7 mg of L-arginine (produced by Sigma-Aldrich, Inc.) was added to the aqueous solvent containing a zinc salt, and 35.9 mg of L-arginine (produced by Sigma-Aldrich, Inc.) was added to the solution of PLGA in DCM.

Example 4 TPM045

20 mL of TuNEX (3.5 mg/mL) was mixed with 4 mL of an aqueous zinc chloride solution (1.0 mg/mL) to obtain a zinc salt of TuNEX. This liquid was centrifuged to separate the zinc salt. The zinc salt was washed with water and then freeze-dried. 302.5 mg of the freeze-dried zinc salt was dispersed in 1.1 mL of water to obtain an aqueous solvent containing the zinc salt. The zinc salt had a mean particle size of about 170 nm. 47.9 mg of L-arginine (produced by Sigma-Aldrich, Inc.) was added to the aqueous solvent containing the zinc salt. The resulting mixture was heated to 40° C., and irradiated with an ultrasonic wave to dissolve the L-arginine and obtain an amino-acid containing S/W suspension. Separate from this, 2,750 mg of a lactic acid-glycolic acid copolymer (PLGA) (produced by Wako Pure Chemical Industries, Ltd., weight average molecular weight: about 10,000, lactic acid:glycolic acid=50:50, containing free carboxyl groups) was dissolved in 5.5 mL of dichloromethane (DCM). Further, 47.9 mg of L-arginine (produced by Sigma-Aldrich, Inc.) was added. The resulting mixture was heated to 40° C., and sonicated to dissolve L-arginine, thus obtaining an amino acid-containing polymer solution.

Subsequently, the S/W suspension was added to the polymer solution, and stirred using a homogenizer to obtain an S/W/O emulsion. Subsequently, the S/W/O emulsion was added to 330 mL of an aqueous solution containing 0.1 w/v % polyvinyl alcohol (PVA), which is a water phase, and the mixture was stirred using a homogenizer to obtain an S/W/O/W emulsion.

The S/W/O/W emulsion was slowly stirred using a paddle mixer at room temperature for 3 hours to evaporate the dichloromethane, washed with water, and then freeze-dried to form a powdery microcapsule formulation.

Comparative Example 1 TP053R

A microcapsule formulation was produced in the same manner as in Example 1 except that 144 mg of L-arginine (produced by Sigma-Aldrich, Inc.) was dissolved in the aqueous solvent containing the zinc salt to obtain an amino acid-containing S/W suspension, and an amino acid-containing polymer solution was obtained without adding L-arginine (produced by Sigma-Aldrich, Inc.) to the solution of PLGA in DCM.

Comparative Example 2 TPM026

20 mL of TuNEX (3.5 mg/mL) was mixed with 4 mL of an aqueous zinc chloride solution (1.0 mg/mL) to obtain a zinc salt of TuNEX. This liquid was centrifuged to separate the zinc salt. The zinc salt was washed with water and freeze-dried. 60 mg of the freeze-dried zinc salt was dispersed in 0.6 mL of water to obtain an aqueous solvent containing the zinc salt. 90 mg of L-arginine (produced by Sigma-Aldrich, Inc.) was added to the aqueous solvent containing the zinc salt. The resulting mixture was heated to 40° C. and sonicated to dissolve L-arginine, thus obtaining an amino-acid containing S/W suspension. Separate from this, 300 mg of a lactic acid-glycolic acid copolymer (PLGA)(produced by Wako Pure Chemical Industries, Ltd., weight average molecular weight: about 10,000, lactic acid:glycolic acid=50:50, containing free carboxyl groups) was dissolved in 6 mL of dichloromethane (DCM) to obtain an amino acid-containing polymer solution. Subsequently, the S/W suspension was added to the polymer solution and stirred using a homogenizer to obtain an S/W/O emulsion. Subsequently, the S/W/O emulsion was added to 660 mL of an aqueous solution containing 0.1 w/v % polyvinyl alcohol (PVA), which is a water phase, and the mixture was stirred using a homogenizer to obtain an S/W/O/W emulsion. The S/W/O/W emulsion was slowly stirred using a paddle mixer at room temperature for 3 hours to evaporate the dichloromethane. The resulting mixture was washed with water and then freeze-dried to form a powdery microcapsule formulation.

Test Example 1

The TuNEX encapsulation efficiency of each of the powdery microcapsule formulations obtained in the Examples and Comparative Examples was calculated. Table 1 shows the TuNEX encapsulation efficiency and L-arginine distribution ratio (molar ratio) of each powdery microcapsule formulation.

TABLE 1

| | L-arginine distribution ratio (L-arginine in S/W suspension phase:L-arginine in polymer solution phase) | Encapsulation efficiency |
|---|---|---|
| Example 1 | 1:1 | 69.5% |
| Example 2 | 1:3 | 38.1% |
| Example 3 | 3:1 | 27.7% |
| Example 4 | 1:1 | 86.3% |
| Comparative Example 1 | 0:1 | 9.6% |
| Comparative Example 2 | 1:0 | 19.0% |

A high TuNEX encapsulation efficiency was achieved by incorporating the arginine into both the S/W suspension phase and the polymer solution phase.

Test Example 2

The powders of Examples 1 and 4 were dispersed in a dispersant, and each dispersion was subcutaneously administered to Lewis male rats with a body weight of 230 to 240 g at a dose of 100 mg/kg. As a control, TuNEX (an aqueous solution) was subcutaneously administered at a dose of 5 mg/kg in a similar manner. As the dispersant, a phosphate buffered saline containing 1.25 w/v % carboxymethyl cellulose and 0.05 w/v % Polysorbate 80 and sterilized with an autoclave was used. TuNEX was administered at a dose of 100 mg/kg. After the administration, blood was periodically collected, and serum TuNEX was measured by ELISA. FIG. 1 shows a pharmacokinetic profile created by plotting the serum TuNEX concentration (μ/mL) versus time after the administration. In both Example 1 and Example 4, an almost constant serum TuNEX concentration was observed over a long period of time.

Test Example 3

The mean particle size of each of the zinc salts of TuNEX obtained by various production methods described in Preparation Examples 1 to 10 below was measured by the aforementioned method. Regarding the zinc salts of TuNEX obtained in Preparation Examples 1, 2, 4, and 5, the relative binding activity of TuNEX upon dissolution of the zinc salts of TuNEX in physiological saline was evaluated.

Preparation Example 1

An aqueous zinc chloride solution (1.0 mg/mL) was slowly added to 1 mL of TuNEX (3.5 mg/mL) while stirring the TuNEX to obtain an insoluble material. The molar ratio of zinc chloride to TuNEX (zinc chloride/TuNEX) was 31. The insoluble material was precipitated by centrifugation (14,000 rpm, 30 min) and separated. This was washed to remove an excess of zinc chloride, etc., and freeze-dried to obtain a powdery zinc salt of TuNEX.

Preparation Example 2

An aqueous zinc chloride solution (1.0 mg/mL) was slowly added to 1 mL of TuNEX (3.5 mg/mL) while stirring the TuNEX to obtain an insoluble material. The molar ratio of zinc chloride to TuNEX (zinc chloride/TuNEX) was 62. The insoluble material was precipitated by centrifugation (14,000 rpm, 30 min) and separated. This was washed to remove an excess of zinc chloride, etc., and freeze-dried to obtain a powdery zinc salt of TuNEX.

Preparation Example 3

Polyvinyl alcohol (PVA) was dissolved in 1 mL of TuNEX (3.5 mg/mL) to a concentration of 0.05 w/v %. While stirring this solution, an aqueous zinc chloride solution (10 mg/mL) was slowly added to obtain an insoluble material. The molar ratio of zinc chloride to TuNEX (zinc chloride/TuNEX) was 63. The insoluble material was precipitated by centrifugation (14,000 rpm, 30 min) and separated. This was washed to remove an excess of zinc chloride, etc., and freeze-dried to obtain a powdery zinc salt of TuNEX.

Preparation Example 4

An aqueous zinc chloride solution (1.0 mg/mL) was slowly added to 1 mL of TuNEX (3.5 mg/mL) while stirring the TuNEX to obtain an insoluble material. The molar ratio of zinc chloride to TuNEX (zinc chloride/TuNEX) was 67. The insoluble material was precipitated by centrifugation (14,000 rpm, 30 min) and separated. This was washed to remove an excess of zinc chloride, etc., and freeze-dried to obtain a powdery zinc salt of TuNEX.

Preparation Example 5

An aqueous zinc chloride solution (1.0 mg/mL) was slowly added to 1 mL of TuNEX (3.5 mg/mL) while stirring the TuNEX, thus obtaining an insoluble material. The molar ratio of zinc chloride to TuNEX (zinc chloride/TuNEX) was 314. The insoluble material was precipitated by centrifugation (14,000 rpm, 30 min) and separated. The precipitate was washed to remove an excess of zinc chloride, etc., and freeze-dried to obtain a powdery zinc salt of TuNEX.

Preparation Example 6

An aqueous zinc chloride solution (50.0 mg/mL) was slowly added to 1 mL of TuNEX (3.5 mg/mL) while stirring the TuNEX to obtain an insoluble material. The molar ratio of zinc chloride to TuNEX (zinc chloride/TuNEX) was 377. The insoluble material was precipitated by centrifugation (14,000 rpm, 30 min) and separated. This was washed to remove an excess of zinc chloride, etc., and freeze-dried to obtain a powdery zinc salt of TuNEX.

Preparation Example 7

An aqueous zinc chloride solution (10.0 mg/mL) was slowly added to 1 mL of TuNEX (3.5 mg/mL) while stirring the TuNEX to obtain an insoluble material. The molar ratio of zinc chloride to TuNEX (zinc chloride/TuNEX) was 628. The insoluble material was precipitated by centrifugation (14,000 rpm, 30 min) and separated. This was washed to remove an excess of zinc chloride, etc., and freeze-dried to obtain a powdery zinc salt of TuNEX.

Preparation Example 8

An aqueous zinc chloride solution (20.0 mg/mL) was slowly added to 1 mL of TuNEX (3.5 mg/mL) while stirring the TuNEX to obtain an insoluble material. The molar ratio of zinc chloride to TuNEX (zinc chloride/TuNEX) was 1,257. The insoluble material was precipitated by centrifugation (14,000 rpm, 30 min) and separated. This was washed to remove an excess of zinc chloride, etc., and freeze-dried to obtain a powdery zinc salt of TuNEX.

Preparation Example 9

An aqueous zinc chloride solution (30.0 mg/mL) was slowly added to 1 mL of TuNEX (3.5 mg/mL) while stirring the TuNEX to obtain an insoluble material. The molar ratio of zinc chloride to TuNEX (zinc chloride/TuNEX) was 1,885. The insoluble material was precipitated by centrifugation (14,000 rpm, 30 min) and separated. This was washed to remove an excess of zinc chloride, etc., and freeze-dried to obtain a powdery zinc salt of TuNEX.

Preparation Example 10

An aqueous zinc chloride solution (40.0 mg/mL) was slowly added to 1 mL of TuNEX (3.5 mg/mL) while stirring the TuNEX to obtain an insoluble material. The molar ratio of zinc chloride to TuNEX (zinc chloride/TuNEX) was 2,514. The insoluble material was precipitated by centrifugation (14,000 rpm, 30 min) and separated. This was washed to remove an excess of zinc chloride, etc., and freeze-dried to obtain a powdery zinc salt of TuNEX.

Table 2 shows the mean particle size of the powdery zinc salts of TuNEX obtained in the above Preparation Examples, and the molar ratio of zinc chloride to TuNEX mixed in the production of each powder.

TABLE 2

|  | Molar ratio of zinc chloride to TuNEX | Mean particle size of zinc salt of TuNEX |
|---|---|---|
| Preparation Example 1 | 31 | 180 nm |
| Preparation Example 2 | 62 | 171 nm |
| Preparation Example 3 | 63 | 750 nm |
| Preparation Example 4 | 67 | 173 nm |
| Preparation Example 5 | 314 | 2,088 nm |
| Preparation Example 6 | 377 | 1,500 nm |
| Preparation Example 7 | 628 | 4,600 nm |
| Preparation Example 8 | 1,257 | 2,700 nm |
| Preparation Example 9 | 1,885 | 1,500 nm |
| Preparation Example 10 | 2,514 | 1,650 nm |

The relative binding activity of TuNEX upon dissolution of the zinc salts of TuNEX obtained in Preparation Examples 1, 2, 4, and 5 in physiological saline were 90%, 100%, 100%, and 100%, respectively.

Example 5 (L-His)

A microcapsule formulation was produced in the same manner as in Example 1 except that the zinc salt of TuNEX was used in an amount of 412.4 mg in place of 550 mg and L-histidine was used in place of L-arginine. The encapsulation efficiency of this microcapsule formulation was determined in the same manner as in Test Example 1 and found to be 43.94%.

Comparative Example 3

A microcapsule formulation was produced in the same manner as in Example 5 except that L-histidine was not added to the solution of PLGA in DCM. The encapsulation efficiency of this microcapsule formulation was determined in the same manner as in Test Example 1 and found to be 5.52%.

Example 6 (HSA)

10 mL of HSA (3.5 mg/mL) was mixed with 2 mL of an aqueous zinc chloride solution (30 mg/mL) to obtain a zinc salt of HSA. This solution was centrifuged to separate the zinc salt, and the zinc salt was washed with water and then freeze-dried. 481.9 mg of the freeze-dried zinc salt was dispersed in 1.1 mL of water to obtain an aqueous solvent containing the zinc salt.

71.8 mg of L-arginine (produced by Sigma-Aldrich) was added to the aqueous solvent containing the zinc salt. This mixture was heated to 40° C. and irradiated with ultrasound to dissolve the L-arginine, thus obtaining an S/W suspension containing an amino acid. Separately, 2,750 mg of a lactic acid-glycolic acid copolymer (PLGA) (produced by Wako Pure Chemical Industries, Ltd., weight average molecular weight: about 10,000, lactic acid/glycolic acid ratio 50:50, including free carboxyl groups) was dissolved in 5.5 mL of dichloromethane (DCM), and 71.8 mg of L-arginine (produced by Sigma-Aldrich) was added. This mixture was allowed to stand overnight to dissolve the L-arginine, thus obtaining an amino acid-containing polymer solution.

Next, the S/W suspension was added to the polymer solution and stirred using a homogenizer (Homogenizer T10) at scale 6 for 1 minute to obtain an S/W/O emulsion. Subsequently, the S/W/O emulsion was added to 330 mL of an aqueous solution of 0.1 w/v % polyvinyl alcohol (PVA), which is an aqueous phase, and the mixture was stirred with a homogenizer (Homogenizer T10) at 18,000 rpm for 3 minutes, thus giving an S/W/O/W emulsion. The S/W/O/W emulsion was stirred with a paddle mixer at 650 rpm at room temperature for 3 hours to remove the dichloromethane by evaporation. The resulting mixture was centrifuged at 6,000 rpm for 2 minutes to recover microcapsules. The microcapsules were washed with water and then freeze-dried to obtain a powdery microcapsule formulation. The encapsulation efficiency of the obtained microcapsule formulation was confirmed in the same manner as in Test Example 1, and was found to be 48%.

Comparative Example 4 (HSA)

A microcapsule formulation was prepared in the same manner as in Example 6, except that L-arginine was not added. The encapsulation efficiency of this microcapsule formulation was measured in the same manner as in Test Example 1, and was found to be 8%.

The invention claimed is:

1. A method for producing a microcapsule formulation comprising:
   step A of adding a basic amino acid to an aqueous solvent containing a heavy metal salt of a peptidic physiologically active substance to obtain an amino acid-containing S/W suspension;
   step B of adding a basic amino acid to an organic solvent containing a biodegradable polymer to obtain an amino acid-containing polymer solution;
   step C of dispersing the amino acid-containing S/W suspension in the amino acid-containing polymer solution, which is an oil phase, to obtain an S/W/O emulsion;
   step D of dispersing the S/W/O emulsion in a water phase to obtain an S/W/O/W emulsion; and
   step E of removing the organic solvent from the S/W/O/W emulsion to obtain the microcapsule formulation.

2. The method according to claim 1, wherein the molar ratio of the basic amino acid contained in the amino acid-containing S/W suspension to the basic amino acid contained in the amino acid-containing polymer solution is 1:5 to 5:1.

3. The method according to claim 1, wherein the heavy metal salt of the peptidic physiologically active substance has a mean particle size of 1 μm or less and is insoluble in both water and organic solvents.

4. The method according to claim 1, wherein the peptidic physiologically active substance has an IgG structure.

5. The method according to claim 1, wherein the peptidic physiologically active substance is TuNEX.

6. The method according to claim 1, wherein the heavy metal salt is a zinc salt.

7. The method according to claim 1, wherein the basic amino acid is L-arginine or L-histidine.

8. The method according to claim 1, further comprising step F of subjecting microcapsules obtained by removing the organic solvent from the S/W/O/W emulsion in step E to freeze-drying or spray-drying to form a powder.

9. The method according to claim 1, wherein the biodegradable polymer is a polylactic acid, a lactic acid-glycolic acid copolymer, or a mixture thereof.

10. The method according to claim 9, wherein the molar ratio of lactic acid to glycolic acid (lactic acid:glycolic acid) in the biodegradable polymer is 99:1 to 50:50.

11. The method according to claim 10, wherein the molar ratio of lactic acid to glycolic acid (lactic acid:glycolic acid) in the biodegradable polymer is 75:25 to 50:50.

12. The method according to claim 1, wherein the biodegradable polymer has a weight average molecular weight of 3,000 to 200,000.

13. The method according to claim 12, wherein the biodegradable polymer has a weight average molecular weight of 3,000 to 50,000.

14. The method according to claim 13, wherein the biodegradable polymer has a weight average molecular weight of 5,000 to 200,000.

15. A microcapsule formulation produced by the method according to claim 1.

* * * * *